United States Patent [19]

Russo

[11] Patent Number: 4,519,796
[45] Date of Patent: May 28, 1985

[54] THORACIC DRAINAGE DEVICE

[76] Inventor: Ronald D. Russo, 8 Candleberry Rd., Barrington, R.I. 02806

[21] Appl. No.: 505,237

[22] Filed: Jun. 17, 1983

[51] Int. Cl.³ .............................................. A61M 1/00
[52] U.S. Cl. .................................................. 604/319
[58] Field of Search ....................... 604/319, 320, 321

[56] References Cited

U.S. PATENT DOCUMENTS

| | | | |
|---|---|---|---|
| 3,363,626 | 1/1968 | Bidwell et al. | 604/321 X |
| 3,363,627 | 1/1968 | Bidwell et al. | 604/321 |
| 3,559,647 | 2/1971 | Bidwell et al. | 604/321 |
| 3,683,913 | 8/1972 | Kurtz et al. | 604/321 |
| 3,861,390 | 1/1975 | Schachet | 604/321 |
| 4,261,362 | 4/1981 | Kurtz et al. | 604/321 X |
| 4,296,748 | 10/1981 | Kurtz et al. | 604/323 X |
| 4,312,351 | 1/1982 | Kurtz et al. | 604/321 X |
| 4,455,141 | 6/1984 | Todd | 604/319 |

Primary Examiner—William H. Grieb
Attorney, Agent, or Firm—Robert J. Doherty

[57] ABSTRACT

This invention relates to a novel and improved thoracic drainage device characterized by drainage directly into an open collection bottle with an inlet connectable to receive air and fluid from the thoracic cavity, an outlet from the bottle connected to a negative pressure relief valve, positive pressure relief valve, a one-way valve, and an adjustable means of suction control. A negative pressure indicator will indicate a rise, fall, or holding pressure within the intra pleural cavity. An air leak detector positioned downstream of the negative pressure indicator and combined with a common baffled reservoir prevents excessive splashing during air leak detection. Both the negative pressure and positive pressure relief valves are located downstream of the reservoir to relieve any pressure build up with the reservoir. The one-way valve is provided after the pressure relief valves to permit the escape of air, but preventing any backflow of air to enter the device. A suction control means is located downstream of the one-way valve to permit regulated suction to be applied to the device.

19 Claims, 3 Drawing Figures

THORACIC DRAINAGE DEVICE

BACKGROUND OF THE INVENTION

Drainage of the thoracic cavity has been accomplished by underwater drainage devices of unitized plastic construction for the past ten years or so. These devices are depicted in the prior art patents of Bidwell, U.S. Pat. Nos. 3,363,626, 3,363,627, and 3,559,647.

These devices use a classical collection chamber, a water seal chamber, and a suction control chamber. One major deficiency of these devices was overcome by Kurtz U.S. Pat. No. 3,683,913 which prevented loss of the water seal by means of a float valve. From this prior art came a commercial product known as the Deknatel Pleurevac A-4000 product which became the standard utilized product until the year 1980. The Pleurevac was favorably received in that it combined the main essential elements of collection, underwater seal, and suction control all in one unitized structure. The Pleurevac A-4000 however suffered some limitations in that it required a considerable amount of water to set up the device, limiting its use in the emergency room. The suction control required continual adding of water, which evaporated during use and it was noisy and disturbed patients. Due to the limitations of the water seal and suction control the A-4000 has to be over 18" in height making it difficult to position on the lower bed rail which is only 12" from the floor.

Attempts to overcome these above indicated deficiencies were proposed by the underwater drainage devices disclosed in recently issued U.S. Pat. Nos. 4,261,362, 4,296,748, and 4,312,351. All three of these patents disclose devices which still use an underwater seal. U.S. Pat. No. 4,261,362 discloses the use of the patient's own drainage to form a seal with dissolvable compartments in the collection chamber. There is no built in suction control. In U.S. Pat. No. 4,296,748 a separate suction control bottle attachable by means of a needle to the device shown in U.S. Pat. No. 4,261,362 was proposed as a necessary means of built in suction control. In both these devices a one-way valve is provided after the water seal to prevent loss of the water seal in the event of high negativity within the patient's pleural cavity. The valve does not and is not intended to act as a replacement for a water seal.

In Kurtz U.S. Pat. No. 4,312,351 an underwater. seal is provided as in U.S. Pat. Nos. 4,261,362 and 4,296,748 however, apparently recognizing that the high-negativity valve can become clogged due to its proximity of the water seal, this valve is isolated away from the body fluid seal to protect its function. None of the devices shown in these patents other than the original A-4000 device have ever been commercialized.

However in 1980, a new device was commercialized, called Thora-Klex, which was developed by two cardiovascular surgeons Doctors Elliott and Halseth. The Thora-Klex product was different than the prior art in that it replaced the water seal with a one-way valve and provided a mechanical suction control means instead of a water suction control means of the Pleurevac A-4000 and the Kurtz and Bidwell patents above described.

Thora-Klex was promoted as a "waterless" thoracic drainage device which was more convenient to set up, less cumbersome, lower in height, and did not have a water seal and did not need water for suction control. Thora-Klex has been well received for use in emergency room situations in that it is easy to set up and does not require water for a water seal or suction control.

While Thora-Klex is an improvement in the state of the art, it suffers from some major deficiencies, both diagnostic and functional in character which makes it limited in use and, accordingly, the Pleurevac device even with its water requirements, is still considered the standard for general purpose nonemergency cardiovascular and thoracic surgery.

SUMMARY OF THE INVENTION

Like Thora-Klex, this invention provides a substantial advancement over the prior art in that it does not have a water seal and does not require water for suction control.

It further eliminates the problems with Thora-Klex making it applicable for all situations of emergency, cardiovascular, thoracic and pediatric cases.

One of the main diagnostic functions of a thoracic drainage unit is to inform the surgeons when the patient's lungs are leaking air. Air leakage informs the surgeon that the lung is not fully closed after surgery and that continual leakage could result in lung collapse or pneumothorax. Thora-Klex provies an integral U-tube in the patient drainage line which theoretically is supposed to replace the air leak detector provided by the Pleurevac water seal. The patient's own pleural drainage is supposed to fill this U-tube if water needs to be added. In actual practice this in line U-tube is virtually useless in providing an accurate means for diagnosing an air leak. Positive pressure from the patient's exhalation readily blows out any retained water in the U-tube. The surgeon is now left with no means for diagnosing an air leak. Water must be continually injected into the U-tube which requires added cost and maintenance. Further when drainage from the pleural space is retained in the U-tube, fluid backs up in the U-tube and patient tube which requires the already weakened patient to exert an abnormally high exhalation pressure to force out this locked in fluid. This is known as patient column build up in the patient drainage tube which can actually induce a collapsed lung, rather than promote expansion of the lung. This is especially true in pediatric cases.

In summary, the Thora-Klex tube indicator is not an efficient air leak diagnosing means and can further prevent efficient and rapid drainage of fluid from the chest into the collection device. The devices proposed in U.S. Pat. Nos. 4,261,362, 4,296,748, and 4,312,351 would also suffer from this column build up problem.

It is further important to provide an indicator means for determining negative pressure. This is diagnostically important such that it informs the user that the lung is expanding and is remaining expanded. Typically as the lung expands, it creates negative pressure. The U-tube has no means for indicating either negative or positive pressure to the surgeon. It is important to know that the lung is maintaining a constant negative pressure and that there are no air leaks being generated from the lung.

The subject invention provides a simple and effective means for providing a negative pressure indicator combined with an effective air leak indicator. Chest drainage is permitted to flow freely down the patient tube directly into the collection chamber. A combination negative pressure indicator and air leak detector is provided downstream of the collection chambers eliminating column buildup and which cannot be blown out by the patient's exhalation. The design of this detector further eliminates another major functional problem of Thora-Klex, which is sticking of the one-way valve which replaces the conventional water seal in Pleure-vac.

The one-way valve seal of Thora-Klex is positioned directly above the fluid collection chambers and is in direct communication with this fluid. The collected body fluids, blood and aerosols that come in contact with the valve have been found to cause contamination and sticking problems with the valve. The valve is so designed to open at low pressures of less than 4 cm $H_2O$ to permit a rapid exit of air out the valve and to minimize any patient exhertion. In the subject invention, the one-way valve is isolated downstream of the combination detector and thus body fluids, etc. cannot reach the valve since the detector protects the valve from contamination and premature sticking problems.

The subject invention further provides a means for preventing loss of the air leak detector due to either extremes of either positive or negative pressure which can be generated by the patient either breathing deeply or a firm cough. A uniquely designed reservoir without the need for a float valve is provided at the top of the negative pressure indicator to prevent fluid loss due to deep breathing of the patient. The air leak detector also has a unique shaped reservoir to prevent loss due to a firm positive pressure cough from the patient. The air leak detector reservoir is further designed to prevent excessive splashing due to patient air leaking or bubbling into the reservoir.

The subject invention further eliminates the potential problems with Thora-Klex due to build-up of positive pressure within the device. In the Thora-Klex a positive pressure relief valve is provided. However, it is positioned downstream of the one-way valve. If the one-way valve sticks closed for any reason, positive pressure would be locked within the device which exerts breathing resistance and prevents proper drainage. If this pressure is permitted to build up, it could present a life threatening situation called tension pneumothorax which means that this positive pressure exerts force back up to the vital lung and heart organs.

In the present invention by positioning a positive pressure relief valve before the one-way valve, any positive pressure buildup will be vented directly to atmosphere. This is the case even if the one-way valve were to stick completely closed such that the device provides maximal patient protection at all times.

Downstream of the one-way valve is positioned a suction control regulator chamber. Connected to this chamber is an outlet port connectable to a source of suction readily available in the hospital. A machined thumb screw is provided to selectively control the level of applied suction and opening the screw outward increases the level of suction. A suction indicator flow tube with a ball indicator is calibrated to indicate the level of applied suction as the screw is adjusted. The tube is calibrated to provide suction from 0 to $-40$ cm $H_2O$ which may be visible to the user by providing a scale, i.e., mounted on the flow tube. A high negative pressure relief valve preferably of the poppet type design is further provided to prevent abnormally high suction levels from being applied to the patient.

Thus it is an object of this invention to provide a new and improved thoracic drainage device. It is a further object of this invention to provide a thoracic drainage device capable of being used in all surgical procedures of emergency, pediatric, cardiovascular and thoracic cases.

It is a further object of this invention to provide a device with direct unobstructive flow of air and fluid directly into a collection bottle in combination with a diagnostically meaningful negative pressure indicator and air leak detector.

It is a further object of this invention to provide a combination negative pressure indicator and air leak detector requiring a minimum of injected priming fluid, i.e., less than 20 cc fluid.

It is a further object of this invention to provide a device wherein the negative pressure indicator and air leak detector cannot be lost due to high negative or positive pressure from the patient.

It is a further object of this invention to prevent fluid loss in the negative pressure indicator and air leak detector if the device is tipped 90 degrss in any direction during set up or patient transport.

It is a further object of this invention to provide a thoracic drainage device wherein the main one-way valve, high negative pressure relief valve, positive pressure relief valve and suction control mechanism are isolated or protected from contamination from body fluids which could cause malfunction.

Additional features and advantages of the present invention will be apparent from a consideration of the following detailed description of the preferred embodiment of the invention in connection with the accompanying drawings.

BRIEF DESCRIPTION OF THE DRAWINGS

In the drawings which illustrate the best mode presently contemplated for carrying out the present invention.

DESCRIPTION OF THE PREFERRED EMBODIMENT

Figure 1:
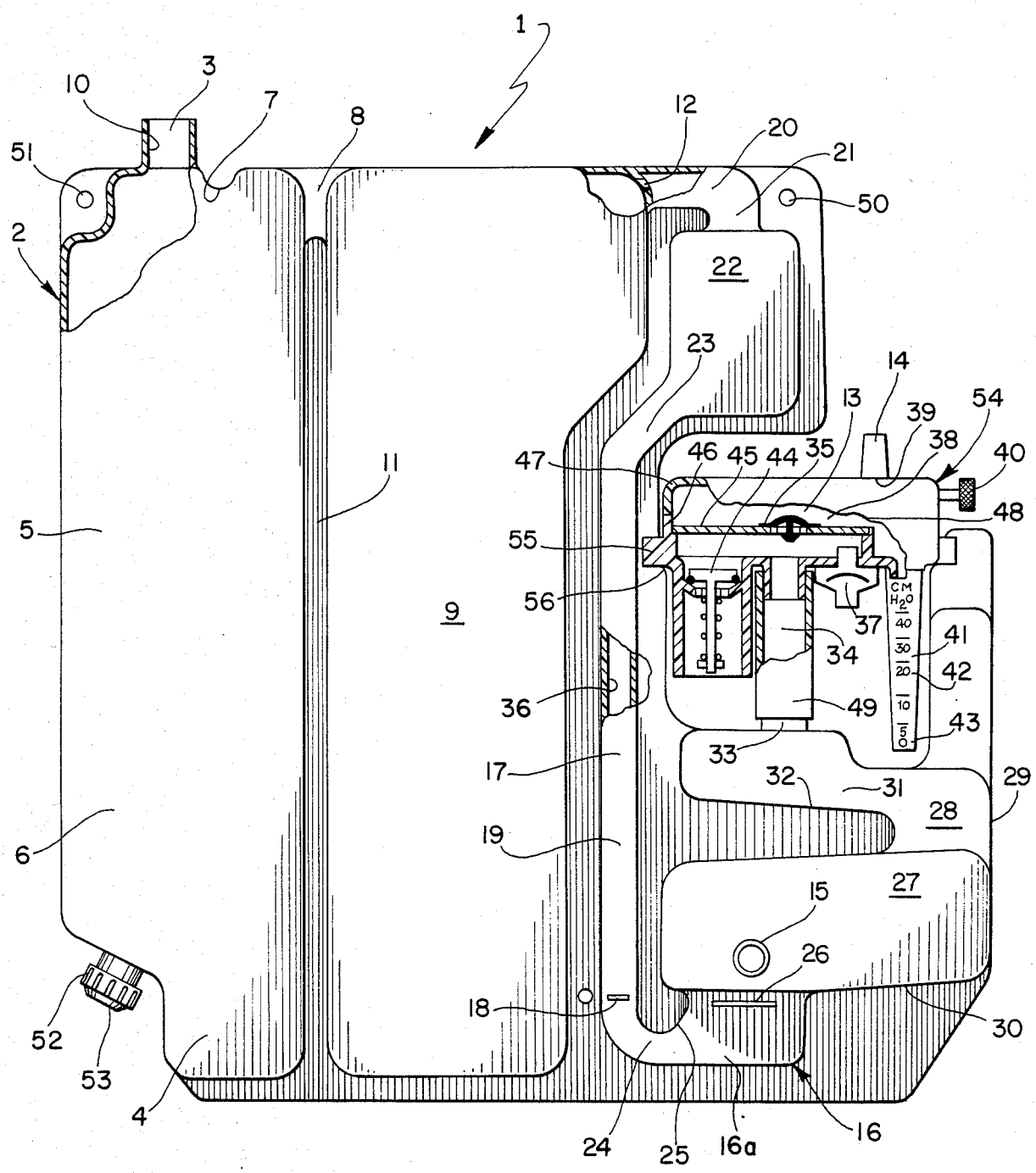
FIG. 1 is a frontal view of the thoracic drainage device of the present invention with parts broken away for clarity.
Figure 2:
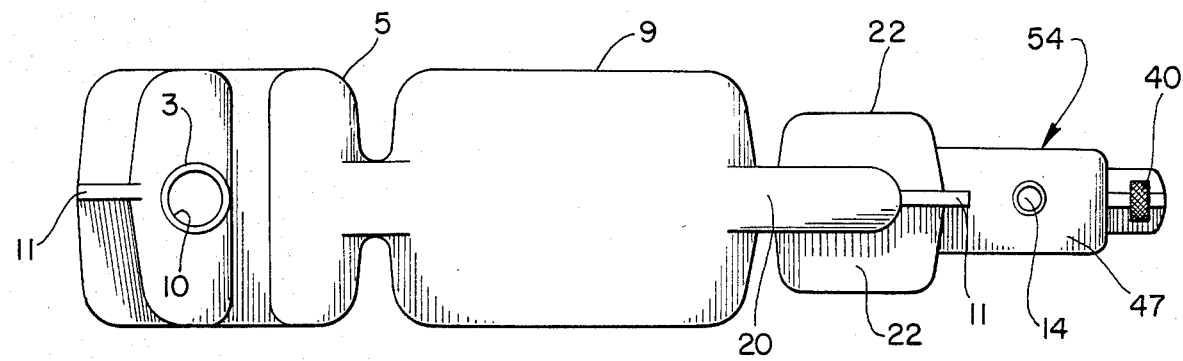
FIG. 2 is a top view of the device.

Referring now to the drawings, there is shown an improved apparatus 1 which has a main collection container 2 which is blow molded or otherwise formed from a clear rigid thermoplastic material such as PETG or polycarbonate. An inlet 3 is provided on the container for connection to a patient tube and a standard chest tube which is in turn connected to the patient's pleural cavity. Air and fluid drained from the pleural cavity initially collect in the lower portion 4 of a first collection chamber 5.

This lower portion 4 is referred to as the pediatric collection chamber since it is the smallest chamber and may be finely graduated to give accurate measurements of collected volume in increments of 1 cc. up to a volume collected of 100 cc. After the pediatric chamber is filled, fluid will continue to collect in first chamber 5 in the upper portion 6 up to an appropriate volume, i.e., 900 cc. A drip ledge 7 is provided to ensure that fluid first collects into first chamber 5 and does not shunt over to the next fluid collection chamber 9. An integral web 11 joins the collection chambers 5 and 9 together. A narrowed passageway 8 is provided at the top portion of the collection chamber 9. This passageway provides the means for transferring fluid and air through the device. As collected fluid builds up in chamber 5, it will have an appropriate total capacity of, i.e., 2,000 cc.

An important feature of collection is that drained fluid will flow directly through inlet opening 10 directly into first chamber 5. There is no U-tube or underwater seal, trap or obstruction to block air or fluid from entering the first chamber. This eliminates any column buildup or backup of fluid into the pleural cavity especially during deep inspirations.

Another important function is that the top passageway 8 permits the transferance of both fluid and air through the device. Air will exit via this passageway through other portions of the device as will hereinafter be explained.

An important feature of the device is that no priming or adding of water is required in order to have the device function once it is attached to the patient. Air will escape through an opening 12 on through the device and out through a main one-way silicone valve 13 and out to atmosphere through an outlet port 14. Upon inspiration, the one-way valve 13 closes preventing back flow of air into the device and onto the patient. This one-way valve action permits immediate re-expansion of the lung. This convenience is especially important in an emergency room situation where time and ease of set up is extremely important.

After initial set up, it is often desirable to be able to monitor air leakage from the patient's pleural cavity as well as monitor negative pressure. The device is provided with a combination air leak detector and negative presure indicator.

Sterile saline solution is injected via syringe and needle through an injection port 15 of conventional construction. A one-time injection of 20 cc. is all that is required. The port is made from a rubber type material which is glued or otherwise attached in place to the container. The injected saline will fall into a lower reservoir 16a of an air leak 16. Fluid will also rise into a negative pressure indicator passage or column 17 which is preferably integrally molded with the body of container 2 until it reaches a zero line 18 on the negative pressure indicator. The chamber 16 lower reservoir 16a, the passage 17 and the zero line 18 calibration define a preset volume, i.e., 20 cc. This one-step injection automatically sets both indicator and detector ready for operation.

With the small amount of water or other appropriate fluid used to prime the indicator (20 cc), the negative pressure indicator will show a rise of fluid in column 19 if the lung is inflating. The negative pressure indicator is not a water seal since negative pressure beyond 10 cm. H₂O will exhaust the 20 cc. water supply. The main one-way valve 13 acts to replace the water seal. In this manner the device can be kept compact in height of only 10½" making it convenient to set up on the lowest rail of a standard hospital bed. Air entering the device will escape through the opening 12 on through a connecting passageway 20 and through an opening 21 into a reservoir 22 out through a lower opening 23 in the reservoir 22 through column 19. The height of the water in the negative pressure indicator at the zero mark 18 is 1 cm. Air leakage will displace the 1 cm. of water and will show up immediately in the lower reservoir of the air leak detector 16. Air will travel around a curved connector 24 and will travel immediately along adjacent surface 25 and will show up on the water surface 26 within the lower reservoir 16a as a very visible air leak bubble.

The air leak detector is provided with an upper larger and horizontally oriented reservoir 27 which captures any splashed or rapidly leaking air bubbling from surface 26 as well as prevent any water loss due to blow out from a patient cough. This larger upper reservoir 27 is further designed that it will trap the injected 20 cc. of filled fluid if the device is tipped in any direction a full 90 degrees. This is sometimes the case if the patient is transported or the device is inadvertently upset. This upper reservoir 27 will return any tipped water such that when the unit is righted again water will fall back down into lower reservoir 16a.

Air leakage can move through an outlet 28 from the upper reservoir 27. This outlet 28 is positioned on the far extreme wall 29 (viewed to the right of FIG. 1) opposite lower reservoir 16 to further prevent splashed fluid from moving out the outlet 28. The lower reservoir 16a is provided with slanted lower wall 30 to permit any splashed fluid to drain down into lower reservoir 16a. Air can thus escape through a passageway 31 which also has a slanted drainage bottom surface or wall 32 and upwardly through an opening 33 into a vertically oriented passageway 34 and out through valve 13.

Valve 13 is an umbrella valve made from compression molded silicone that has a very low opening pressure of i.e., less than 2 cm. H₂O. The valve will reseat itself on seat 35 preventing influx of air when negative pressure is applied by the patient's inspiration. The valve 13 may also be coated with a light film of silicone oil to further aid in sealing. As the patient's air leak in the lung is healing, the negative pressure will become more negative. Along with this healing will be a decrease in the air leak. It is therefore diagnostically important to be able to have an indication of the negative pressure along with a reading of the air leak to determine patient healing or progress. It is therefore an important feature of the device to provide this combination measurement in a valve seal device. As intra pleural cavity pressure increases, the negative pressure indicator will indicate a rise in column 19 and reduced or no leakage in detector 16. A suitable internal diameter of the bore 36 of the pressure indicator column 19 has been found to be 5/16" or 0.312".

The negative pressure indicator will continue to rise slowly until the lung reaches a fully expanded state. When the lung is fully expanded, the fluid level will be maintained at a steady state level. This steady state level in the negative pressure indicator coupled with no bubbles in the air leak detector confirms to the surgeon that the lung is fully expanded and is healed. This is diagnostically important to the surgeon.

The invention gives further reassurance that the healing has remained steady and intact. If the fluid were to fall suddenly in column 19, it would show that an air leak has reoccured and that the intra pleural pressure is dropping. This feature prevents premature assumptions that lung healing is sustained since spontaneous air leaks can occur at any time especially after an initial expansion of the lung. Fluid will rise very slowly in column 19 due to the checking action of the one-way valve 13. This prevents any sudden surges or losses of fluid as is the case in water seal type devices. Reservoir 22 is simply provided to retain any fluid which happens to rise in column 19 if the patient is taking extreme deep breathing exercises. One-way valve 13 further prevents the influx of any air into the column 19 to eliminate the need for any check valve in reservoir 22 as would be the case in a water seal device.

Another important feature of the subject device is the provision of a positive pressure relief valve 37 positioned between the air leak dectector 16 and the one-way silicone valve 13. The valve 37 may be of the silicone disk type on a conical seat which opens at a pressure above that of the one-way valve, i.e., about 5 cm H₂O pressure. This valve 37 is provided to relieve any positive pressure buildup within the device. Having valve 37 upstream of one-way valve 13 always insures that any positive pressure within the device will always be vented to atmosphere especially under heavy repeated coughs by the patient.

Downstream of valve 13 a closed chamber 38 is provided. A screw 40 selectively opens or closes an opening 39 to such chamber 38. As it is sometimes desirable to apply suction to the device to further aid in expansion of the lungs, a suction line is typically connected to an outlet stem 14 connected to opening 39 and suction is controlled by regulation of the screw 40. The actual level of suction applied can be read directly on a flow tube 41 provided with a scale 42. As suction is applied, a stainless steel ball 43 about 0.125" in diameter will rise in the flow tube 41. Opening screw 40 will cause ball 43 to rise in the tube which will indicate the applied suction to the patient. The scale may conveniently read in suction from zero to 40 cm H₂O.

In those cases where suction above the 40 cm H₂O level is applied to the device, there is provided a high negative relief valve 44. This valve will open to atmosphere when suction is applied above 40 cm H₂O. Valve 44 is of the standard spring loaded poppet valve design. Valve 44 is also located upstream of one-way valve 13 to eliminate any pressure buildup within the device. Valve 13 is mounted on a molded generally flat plastic plate 45 which is solvent cemented to a lower plastic housing 46. Lower housing 46 is in turn solvent bonded to upper plastic housing 47 at a joint or seam 48. This entire control assembly 54 is connected to opening 33 by a rubber connecting tube 49. In this manner the control assembly 54 can be easily removed from and connected to the container body 2. In this regard, a bifurcated tongue 55 engages the web 11 above a stop 56 to insure proper positioning.

Figure 3:
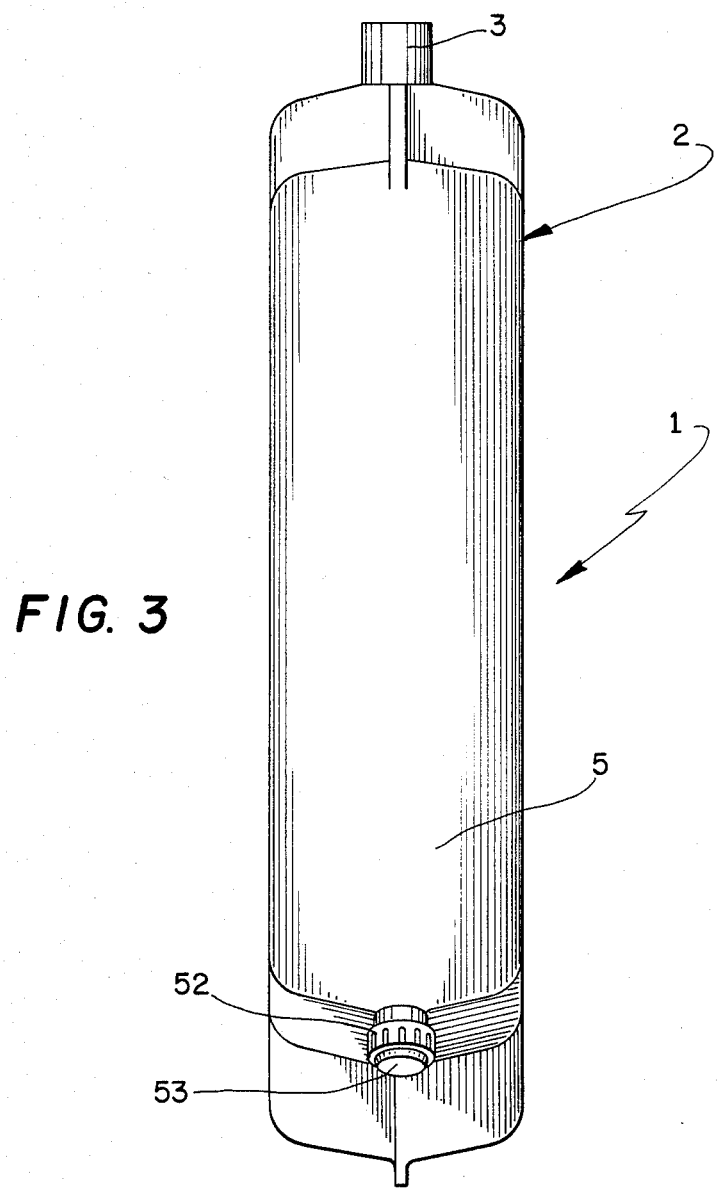
FIG. 3 is a side view of the device.

Holes 50 and 51 are provided in the corners of the container body 2 to accept metal hooks (not shown) for hanging or attachment of the device to the bed or bed rails. In FIG. 3 is shown removable screw cap 52 which has an integral puncturable seal 53 which provides for sampling of fluid collected in first chamber 5 by syringe and needle or emptying by removing cap 52.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An apparatus for draining a patient's chest cavity comprising a body including a closed collection chamber having an inlet at the upper end thereof for connection to a patient drainage tube permitting chest cavity fluid and air to drain directly through said inlet to provide direct unobstructed flow of air and fluid into said collection chamber, an air space above the collection chamber, an outlet from the collection chamber in communication with the air space, said body further including a combination negative pressure indicator and air leak detector assembly in turn including a reservoir positioned downstream of said collection chamber and having a liquid trap portion for receipt of an indicator fluid, said reservoir connected to said collection chamber by an upright column positioned intermediate said collection chamber and said reservoir and in turn connected to said outlet at the upper end thereof and to said liquid trap portion at the lower end thereof, and one-way valve seal downstream of the negative pressure indicator and air leak detector assembly acting as a seal to prevent air from entering back into the air leak detector but permitting air from the air leak detector to flow out the valve seal.

2. The apparatus according to claim 1, including means provided in the reservoir to stop spilling or loss of indicator liquid when the apparatus is tilted up to 90 degress in any direction such that all indicator liquid is returned to the reservoir once the apparatus is righted to its original upright position.

3. The apparatus according to claim 1, including means downstream of the one-way valve seal comprising a flow control valve connectable to a source of external suction, said flow control valve being operable to selectively control the level of suction being applied upstream of the one-way valve seal.

4. An apparatus for draining the chest cavity according to claim 3, wherein a positive pressure relief valve is provided.

5. An apparatus for draining the chest cavity according to claim 3, wherein a high negative suction relief valve is provided.

6. An apparatus for draining the chest cavity according to claim 1, wherein said collection chamber is a plurality of connected chambers.

7. An apparatus for draining the chest cavity according to claim 6 wherein the first collection chamber has finer graduations than succeeding collection chambers.

8. An apparatus for draining a patient's chest cavity comprising a body including a closed collection chamber having an inlet at the upper end thereof for connection to a patient drainage tube permitting chest cavity fluid and air to drain directly through said inlet to provide direct unobstructed flow of air and fluid into said collection chamber, an air space above the collection chamber, an outlet from the collection chamber in communication with the air space, said body further including an air leak detector in turn including a reservoir positioned downstream of said collection chamber and having a liquid trap portion for receipt of an indicator fluid, a first one-way valve seal downstream of the air leak detector acting as a seal to permit air from the air leak detector to escape, yet preventing reverse flow of air from entering the air leak detector, a second one-way valve in parallel air communication with said first one-way valve seal to permit the escape of any positive pressure air within the apparatus directly to atmosphere should positive pressure build up within the apparatus to a level exceeding the opening pressure of the first one-way valve seal, yet prevent any influx of air to enter the apparatus, means downstream of the first one-way valve seal comprising a flow control valve connectable to a source of external suction, said flow control valve being operable to selectively control the level of suction being applied upstream of the one-way valve seal.

9. The apparatus according to claim 8, said first one-way valve seal opening at less than about 5 cm H$_2$O pressure.

10. The apparatus according to claim 8, including means provided in the reservoir to stop spilling or loss of indicator liquid when the apparatus is tilted up to 90 degrees in any direction such that all indicator liquid is returned to the reservoir once the apparatus is righted to its original upright position.

11. An apparatus for draining the chest cavity according to claim 8 wherein said collection chamber is made from a plurality of connected chambers.

12. An apparatus for draining the chest cavity according to claim 11 wherein the first collection chamber of the plurality of chambers has finer graduations than succeeding chambers.

13. An apparatus for draining the chest cavity according to claim 8 wherein a high negative suction relief valve is provided.

14. An apparatus for draining the chest cavity according to claim 8 wherein means are provided to attach the apparatus to a bed rail.

15. An apparatus for draining the chest cavity comprising a body including a closed collection chamber having an inlet at the upper end thereof for connection to a patient drainage tube permitting fluid and air to drain directly through said inlet to provide direct, unobstructed flow of air and fluid into said collection chamber, an air space above the collection chamber, an outlet from the collection chamber in communication with the air space, said body further including an air leak detector in turn including a reservoir positioned downstream of said collection chamber and having a liquid trap portion for receipt of an indicator fluid, said air leak detector downstream of and in air communication with said outlet, means provided in the reservoir to prevent spilling or loss of detector liquid when the apparatus is tilted such that indicator liquid returns to the reservoir once the apparatus is righted to its original pretilt position, an air space above the reservoir, a second outlet from said air space, two one-way valves positioned downstream of said outlet and in air communication with said second outlet, one of said valves acting as a one-way seal to permit air from said air leak detector to escape yet prevent reverse flow of air from entering the air space above the air leak detector, said second valve in parallel air communication with the first one-way valve seal to permit the escape of any positive pressure from the air space outlet to exit directly to atmosphere yet prevent any influx of air to enter the air space, both valves opening at less than about 10 cm H$_2$O pressure, means downstream of the first one-way valve seal comprising a flow control valve connectable to a source of external suction, said flow control valve being operable to selectively control the level of suction being applied upstream of both said one-way valves.

16. An apparatus for draining the chest cavity according to claim 15 wherein said collection chamber is made from a plurality of chambers.

17. An apparatus for draining the chest cavity according to claim 16 wherein the first drainage collection chamber has finer graduations than succeeding chambers.

18. An apparatus for draining the chest cavity according to claim 15 wherein a high negative suction relief valve is provided.

19. An apparatus for draining the chest cavity according to claim 16 wherein means are provided to attach the apparatus to bed rails.

* * * * *